(12) United States Patent  
Klein

(10) Patent No.: US 9,897,577 B2  
(45) Date of Patent: Feb. 20, 2018

(54) APPARATUS FOR FIELD-FLOW FRACTIONATION

(71) Applicant: Postnova Analytics GmbH, Landsberg (DE)

(72) Inventor: Thorsten Klein, Schondorf (DE)

(73) Assignee: Postnova Analytics GmbH, Landsberg (DE)

( * ) Notice: Subject to any disclaimer, the term of this patent is extended or adjusted under 35 U.S.C. 154(b) by 234 days.

(21) Appl. No.: 14/796,055

(22) Filed: Jul. 10, 2015

(65) Prior Publication Data

US 2016/0011155 A1    Jan. 14, 2016

(30) Foreign Application Priority Data

Jul. 10, 2014  (DE) .......................... 10 2014 213 428

(51) Int. Cl.
  *G01N 1/00*  (2006.01)
  *G01N 30/32*  (2006.01)
  (Continued)

(52) U.S. Cl.
  CPC ......... *G01N 30/32* (2013.01); *G01N 30/0005* (2013.01); *G01N 30/38* (2013.01);
  (Continued)

(58) Field of Classification Search
  CPC ........ G01N 30/32; G01N 30/34; G01N 30/20; G01N 2030/202; G01N 2030/027
  (Continued)

(56) References Cited

U.S. PATENT DOCUMENTS 5,160,625 A * 11/1992 Jonsson ................. B01D 43/00  
  210/198.2  
2004/0000519 A1 * 1/2004 Jiang ................... G01N 30/0005  
  210/634

(Continued)

FOREIGN PATENT DOCUMENTS

DE         68921458         11/1995  
DE       102011076230        2/2012  
  (Continued)

*Primary Examiner* — Eric S McCall  
*Assistant Examiner* — Mohammed E Keramet-Amircola  
(74) *Attorney, Agent, or Firm* — Hodgson Russ LLP

(57) ABSTRACT

The present invention relates to an apparatus for field-flow fractionation and to a method for separating samples by means of field-flow fractionation using this apparatus. The apparatuses of the invention comprise one or more reservoirs, a pump, a first flow volume splitting device, two valves for flow control, an injector, a separation channel having a first connector at a first end and a second connector at a second end or an AF4 separation channel having a first connector at a first end, a second connector at a second end and a third connector between the first and the second ends, optionally a second flow volume splitting device, a back-pressure element, one or more detector(s), a flow volume control device and one or more waste container(s). The apparatuses of the invention are characterized in that they comprise a valve for flow control in a first flow path and a second flow path which connect the pump to the first or the second or the third connector of the separation channel and that these valves are switched alternately in a controllable time ratio.

25 Claims, 3 Drawing Sheets

(51) Int. Cl.
*G01N 30/00* (2006.01)
*G01N 30/38* (2006.01)

(52) U.S. Cl.
CPC . *G01N 2030/324* (2013.01); *G01N 2030/326* (2013.01); *G01N 2030/328* (2013.01)

(58) Field of Classification Search
USPC .......................................................... 73/61.56
See application file for complete search history.

(56) References Cited

U.S. PATENT DOCUMENTS

| | | | | |
|---|---|---|---|---|
| 2005/0148064 | A1* | 7/2005 | Yamakawa | B01L 3/502753 435/287.2 |
| 2008/0264792 | A1* | 10/2008 | Moon | B01D 63/02 204/452 |
| 2011/0042605 | A1* | 2/2011 | Gyger | F16K 1/42 251/333 |

FOREIGN PATENT DOCUMENTS

| | | |
|---|---|---|
| DE | 102010041222 | 3/2012 |
| EP | 1879025 | 1/2008 |
| WO | 2012038518 | 8/2012 |

\* cited by examiner

Detector diagram

1          Monomer
2          Trimer

APPARATUS FOR FIELD-FLOW FRACTIONATION

TECHNICAL FIELD

The present invention relates to an apparatus for field-flow fractionation and a method for the separation of samples by means of field-flow fractionation using said apparatus.

PRIOR ART

Field-flow fractionation (FFF) is a quasi-chromatographic method of analysis for separating macromolecular and colloidal samples. As opposed to chromatography, the separation of samples in field-flow fractionation does not take place in a packed column, but in an open separation channel which does not contain a stationary phase.

Owing to the low height of the channel, a laminar flow with a parabolic flow profile is formed within the channel. Separation of the samples is carried out by a force field which is arranged vertically to this flow within the channel. Under the influence of the applied force field and the counter-acting diffusion of the sample particles, the individual components of the sample are separated. First, a state of equilibrium will occur in which the individual sample components are present in the separation channel in separate layers with a certain layer thickness. Smaller particles with a larger diffusion coefficient reach layers in a higher position, i.e. at a greater distance from the channel wall, and thus regions of higher flow rates. These particles eluate first. Larger particles with a lower diffusion coefficient move in layers that are therefore further down, i.e. closer to the channel wall, and are thus in regions with a lower flow rate with the result that they eluate later.

Depending on the manner in which the force field used is generated, i.e. the physical nature of this field, different field-flow fractionation techniques have been developed. These comprise flow field-flow fractionation, sedimentation field-flow fractionation, such as centrifugal field-flow fractionation, and thermal field-flow fractionation. Among these, flow field-flow fractionation with the sub-techniques of symmetrical flow field-flow fractionation, asymmetrical flow field-flow fractionation (AF4) and hollow-fiber flow field-flow fractionation (HF5) is the most common.

The flows or volume flows required in apparatuses for flow field-flow fractionation are generated by means of conventional HPLC pumps/fluidic pumps. For this purpose, systems comprising at least two pumps or only one pump such as described in WO 2012/038518 are used. In the systems comprising only one pump described in WO 2012/038518 suitable switching means are additionally used within the individual flow paths.

For high-resolution AF4 and HF5 separations, "focusing", i.e. concentration of the sample to form a narrow band in the separation channel, is required first. To achieve this, a carrier liquid, i.e. a solvent, is pumped into the separation channel both through the inlet and through the outlet, the sample being focused in the region where the solvent streams meet in the channel. After focusing is completed, the sample is then eluted from the separation channel and can be detected.

If it is intended to generate the focus flow, i.e. the flow for focusing, by means of only one pump, the pump flow must be divided, i.e. split. Conventional devices for separating the flow volume always work with the separation of a given volume flow between the respective flow paths, continuously splitting the flow on a percentage basis, for example between a first flow path and a second flow path. Depending on the desired separation method, it may be required, however, to keep the flow constant over the first flow path and, at the same time, to change the flow rate in the second flow path so that the total volume of the flow changes during measurement.

To achieve this, suitable mass flow controllers may be used. These usually have a measuring device for measuring the flow, i.e. the volume flow, and a control valve which, depending on a comparison of the target/actual value, is opened or closed to such a degree that the desired volume flow is applied.

The main problem of mass flow controllers is the limited dynamic region for the flow rates, the delayed response time for flow rate control and the limited range of the working pressure in which mass flow regulators may be used. Moreover, mass flow regulators are sensitive to flow rates if the pressure in an AF4 separation system changes during flow control.

As a rule, the control valves used need a pressure difference between inlet and outlet of at least 3 to 10 bar so as to be able to work correctly. In addition, a suitable valve nozzle must be preselected so as to permit accurate adjustment of the desired flow rates at a given valve lift.

Therefore, comparatively high technical effort was required until now to be able to use these mass flow regulators. In doing so, attempts were made to compensate for problems with regard to the dynamic pressure range with the aid of needle valves instead of magnetic valves (cf., for example, the apparatuses described in WO 2012/038518). In doing so, only the measuring device of the respective mass flow regulator was used. However, the needle valves required additional electronic components and a motor for control which meant extra components and thus extra cost. Moreover, the use of needle valves increases the risk of failure as needle valves can easily get caught in the valve seat once they are fully closed. In addition, needle valves tend to be soiled easily so that it will eventually become impossible to adjust the desired flow rates accurately.

The object of the present invention is to provide an improved apparatus for flow field-flow fractionation which is characterized by a simplified design, can be operated without using an additional pump or an additional flow controller and other elements for flow control and requires operating pressures of the fluidic pump used that are less high. The purpose is to significantly reduce the cost and the space requirements for the apparatuses.

Illustration of the Invention

This object is achieved by the apparatuses of the present invention. The apparatuses of the invention are based on a novel flow scheme comprising only one pump and two valves which do not require a mass flow regulator for splitting the pump flow. The most recent developments in the area of high pressure valve technology permit extremely short switching times at high clock rates. Typical switching times required for opening and closing the valves to allow their use in a system for flow field-flow fractionation are in the range from 200 to 400 µs at clock rates of 300 Hz.

In the past, efforts were made to avoid pulsation (i.e. sudden changes in pressure) in the respective flow paths in chromatographic methods of analyses, such as HPLC and quasi-chromatographic methods of analysis such as field-flow fractionation as a matter of principle. Therefore, sequential splitting of the flows by means of the alternating actuation of suitable switching valves was ruled out in the past. However, the newest valve technology permits clocking at such high speeds that the pulsations resulting from switching the valves are compensated by the inertia of the system. Therefore, sequential splitting of the flows in systems for flow field-flow fractionation is an innovation.

Sequential splitting of the flows by means of suitable valves permits doing without the use of mass flow regulators. Instead, the flow split between the individual flow paths is achieved by the chronologically co-ordinated clocking of the switching of two valves in the apparatuses of the invention (one each in a first and a second flow path). In particular, the new flow scheme solves the problems described above in connection with the use of mass flow regulators with regard to the dynamic flow rate range and the necessary operating pressure as well as the flow rate sensitivity. This permits realizing a programmable focus flow with a concomitant reduction in components, resulting in a decrease of cost and the risk of failure.

Nor do the apparatuses of the invention therefore need additional switching valves or back-pressure elements in the respective flow paths connecting the pump to the channel which also leads to simplification of the design and cost reduction.

An additional advantage of sequential splitting of the flows is the improved recovery of the samples. During conventional focusing by continuous flows, the sample is pressed to the semi-permeable membrane along a line in the separation channel with a comparatively high force. This results in interactions of the sample with the membrane so that parts of the sample adhere to the membrane and thus can no longer be eluted. This effect is reflected in the so-called recovery and, depending on the sample/solvent matrix, may only be 67% of the injected volume. This makes precise statements about the sample concentration difficult. Due to sequential splitting of the flows, the sample remains mobile during focusing in the vicinity of the focusing line. This reduces adherence of the sample to the membrane, and a higher degree of recovery can be achieved.

Another advantage of sequential splitting of the flows is the prevention of aggregate formation by focusing. The components of the sample are, in part, concentrated in a very small space during focusing. As a result, a large number of samples tend to form aggregates. This means that the components of the sample aggregate to form a larger molecule or a larger particle. Due to sequential splitting of the flow, the sample remains mobile in the vicinity of the focusing line. This prevents pronounced concentration of the samples on the focus line and thus reduces the risk of aggregate formation.

The apparatuses of the invention are apparatuses for field-flow fractionation.

In a first embodiment, the apparatuses for field-flow fractionation according to the invention comprise one or more reservoirs, a pump, a first flow volume splitting device, a first valve, an injector, a separation channel with a first connector at a first end and a second connector at a second end, a second flow volume splitting device, a second valve, a back-pressure element, one or more detector(s), a flow volume control device and one or more waste containers, wherein
    the first flow volume splitting device is suitable to split the volume flow generated by the pump into a first flow path connecting the pump to the first connector of the separation channel and a second flow path connecting the pump to the second connector of the separation channel,
    the injector is arranged in the first flow path,
    the second flow volume splitting device is arranged within the second flow path and is suitable to split the volume flow of the second flow path between the second connector of the separation channel and the detector(s),
    the back-pressure element is arranged in a third flow path connecting the second flow volume splitting device and the detector(s),
    the flow volume control device is arranged in a fourth flow path which is connected to the separation channel via a further connector; and
    the waste container(s) is/are arranged behind the detector(s) and the volume flow control device,
characterized in that the first valve is arranged in the first flow path between the first flow volume splitting device and the injector, and the second valve is arranged in the second flow path between the first flow volume splitting device and the second flow volume splitting device.

In an alternative embodiment, the apparatuses for field-flow fractionation of the invention comprise one or more reservoirs, a pump, a flow volume splitting device, a first valve, an injector, a separation channel for asymmetrical flow field-flow fractionation (AF4) having a first connector at a first end, a second connector at a second end and a third connector between the first end and the second end of the separation channel, a second valve, a back-pressure element, one or more detector(s), a flow volume control device and one or more waste containers, wherein
    the first flow volume splitting device is suitable to split the volume flow generated by the pump into a first flow path connecting the pump to the first connector of the separation channel and a second flow path connecting the pump to the third connector of the separation channel,
    the injector is arranged in the first flow path,
    the back-pressure element is arranged in a third flow path connecting the second connector of the separation channel to the detector(s),
    the flow volume control device is arranged in a fourth flow path connected to the separation channel via a further connector, and
    the waste container(s) is/are arranged behind the detector(s) and the volume flow control device,
characterized in that the first valve is arranged in the first flow path between the first flow volume splitting device and the injector, and the second valve is arranged in the second flow path between the flow volume splitting device and the third connector of the separation channel.

The invention further relates to a method for analyzing a sample by means of field-flow fractionation using the apparatuses of the invention which comprises the following steps:
(i) injection of a sample into the separation channel using a solvent,
(ii) focusing the sample with the aid of the solvent in the separation channel, and
(iii) elution of the sample with the solvent from the separation channel under the influence of a separation field and detection of the separated sample with one or more detector(s),
and characterized in that the first valve and the second valve of the apparatuses of the invention are opened and closed alternately during focusing in step (ii), the opening time of the first valve being shorter than the opening time of the second valve.

Finally, the invention relates to the use of the apparatuses of the invention in a method for analyzing a sample by means of field-flow fractionation.

In connection with the present invention, the term "injection" means introducing the sample into the solvent by means of the injector of the apparatuses of the invention and flushing the sample into the separation channel together with the solvent.

In connection with the present invention, the term "focusing" means concentration of the sample to form a narrow band in the separation channel. During focusing, solvent in the apparatuses of the invention according to the first embodiment described above is pumped into the separation channel through the first connector and through the second connector of the separation channel and, in the apparatuses of the invention according to the alternative embodiment described above, through the first connector and through the third connector of the separation channel. The sample is focused in the region of the colliding solvent streams in the separation channel, usually at the front end of the separation channel.

In a preferred embodiment of the method of the invention, the flow rate in the first flow path of the apparatuses of the invention while the sample is injected and focused is 0.01 ml/min to 0.5 ml/min.

In connection with the present invention, the term "elution" means flushing the sample out of the separation channel in the direction of the detector(s) with the aid of the solvent, wherein no flow takes place through the second flow path and flushing is carried out under the influence of a separation field the strength of which may be varied depending on the type of the sample to be analyzed.

The first valve of the apparatuses of the invention arranged in the first flow path is permanently open throughout elution, while the second valve in the second flow path is permanently closed and thus no solvent flows through the second flow path. This makes sure that only the pump is responsible for adjusting the flow rate in the first flow path during elution.

The separation field applied during elution and detection is a liquid stream (cross-flow) which is generated vertically to the flow direction of the solvent in the separation channel with the aid of the flow volume control device connected to the separation channel. In addition, it is possible to vary the cross-flow and thus the strength of the separation field with the aid of the flow volume control device.

In connection with the present invention, the term "detection" means detecting the sample in the solvent by means of the detector(s) used and generating a corresponding measuring signal by the sample when this is guided through the detector(s) with the aid of the solvent.

In connection with the present invention, the term "volume flow" means the volume of a solvent flowing through the apparatuses of the invention or parts thereof per time unit, such as the first and/or second flow volume splitting device, the first and/or second valve, the flow volume control device, the separation channel, the back-pressure element and the detector(s). In the following, the term "flow rate" will also be used instead of the term "volume flow".

The liquid and volume flows required for injection, focusing as well as elution and detection in steps (i), (ii) and (iii) of the method of the invention in the apparatuses of the invention according to the first embodiment are generated and controlled by means of the pump and the first and second flow volume splitting devices, the first and second valves, the flow volume control device and the back-pressure element.

The liquid and volume flows required for injection, focusing as well as elution and detection in the steps (i), (ii), and (iii) of the method of the invention in the apparatuses of the invention according to the alternative embodiment are generated and controlled by means of the pump and the flow volume splitting device, the first and the second valves, the flow volume control device and the back-pressure element.

In connection with the present invention, the term "analysis" means fractionating and detecting a sample by field-flow fractionation using the apparatuses of the invention.

In connection with the present invention, the term "sample" means any kind of analyte that may be fractionated and detected by means of the apparatuses of the invention. These can be substances of a molecular weight of 500 Da to 16 MDa or a size of 2 nm to 5 μm which are present in the solvent used either in a dissolved or a suspended form.

In particular, the term "sample" also comprises mixtures wherein the molecular weight and/or the size of the individual components may be the same or different.

Samples for fractionation and detection by means of the apparatuses of the invention are, for example, proteins from the field of the pharmaceutical industry and research, nanoparticles and carbon nano-tubes as well as natural and synthetic polymers, especially silicates, pigments, colloids, peptides, virus cells, liposomes, antibodies, polysaccharides and other macromolecules.

The apparatuses of the invention may comprise one or more reservoir(s) for one or more carrier liquid(s), i.e. for one or more solvents. Measurements in the apparatuses of the invention are preferably carried out with one solvent so that the apparatuses of the invention comprise one reservoir in a preferred embodiment. Alternatively, operation with more than one solvent is possible so that gradient elution can be carried out. In a further embodiment, the apparatuses of the invention therefore comprise two or more reservoirs.

Aqueous and non-aqueous organic solvents may be used as solvents in the apparatuses of the invention. Examples comprise aqueous solvents with 0.5 to 5 g/l NaCl and/or 0.1 to 5 g/l sodium dodecyl sulfate (SDS) and the organic solvents tetrahydrofurane (THF), toluene, acetone, methanol, ethanol, chloroform, dimethyl formamide (DMF) and dimethyl sulfoxide (DMSO) and mixtures thereof.

Any fluidic pump suitable for use in field-flow fractionation or liquid chromatography (LC) may be used as the pump in the apparatuses of the invention. Preferably an HPLC pump is used. The pump is provided for conveying the solvent at a defined constant flow rate.

The apparatuses of the invention comprise only one, i.e. no other, pump for conveying the solvent.

The flow volume splitting devices suitable for use in the apparatuses of the invention are, for example, a T-connector or a manifold.

All commercial T-connectors and manifolds that are suitable for installation in a field-flow fractionation system and/or an HPCL plant may be employed as the T-connectors or manifolds in the apparatuses of the invention. Any material may be used that is inert against the respective solvent and the sample to be analyzed. For example, T-connectors or manifolds of metal or PEEK may be used.

The bore holes in the T-connector or the manifold used as the first flow volume splitting device and the T-connector or the manifold used as the second flow volume splitting device may be of the same size and have an internal diameter of 100 μm to 1,000 μm maximum and preferably 500 μm.

In a preferred embodiment, the bore hole in the T-connector or the manifold used as the first flow volume splitting device has a larger internal diameter than the bore hole in the T-connector or manifold used as the second flow volume splitting device. The internal diameter of the bore hole within the T-connector or the manifold used as the first flow volume splitting device in this preferred embodiment is 500 µm to 1,000 µm maximum and preferably 1,000 µm. The bore hole in the T-connector or the manifold used as the second flow volume splitting device in this preferred embodiment has an internal diameter of 125 µm up to 250 µm maximum and preferably 250 µm. This ensures that the dead volume is as small as possible. Bore holes in the T-connector or the manifold used as the second flow volume splitting device with an internal diameter of more than 250 µm may result in broadening of the peaks and hence affect the measured value.

In a preferred embodiment, the first flow volume splitting device and the second flow volume splitting device is a T-connector each.

High-pressure micro-valves suitable for installation in a field-flow fractionation system and/or an HPLC plant may be used as the valves in the apparatuses of the invention. In principle, these micro-valves are magnetically controlled check valves. The micro-valves can operate at pressures of up to 300 bar and have switching times in the range from 200 to 400 µs. It is possible to achieve a clocking of 300 Hz with these valves. This permits alternating opening and closing of each of the valves with opening times of the valves in the millisecond range. In a preferred embodiment, the micro-valves have a ruby ball as the mobile valve element and a sapphire valve seat. Suitable micro-valves are described, for example in US 2011/042605.

In a preferred embodiment of the apparatuses of the invention with one valve for flow control per first and per second flow path, the flow rate in the first flow path during injection of the sample and its focusing is 0.01 ml/min to 0.5 ml/min. After the sample has been injected and focused, i.e. during elution, the two valves are no longer needed for flow control, i.e. for controlling the volume flows. Therefore, the first valve in the first flow path is kept permanently open for elution, while the second valve in the second flow path is kept permanently closed.

The flow volume control device has the purpose of generating and controlling the cross-flow and is either a syringe pump system or a mass flow controller.

A syringe pump system suitable for use in the apparatuses of the invention comprises two syringes working in a pendulum mode. This prevents uncontrolled discharge of the cross-flow from the separation channel.

In a preferred embodiment, the flow volume control device is a syringe pump system comprising two syringes working in a pendulum mode or a mass flow controller comprising a measuring unit, a control valve and a control wire.

In a particularly preferred embodiment, a syringe pump system comprising two syringes operating in a pendulum mode is used as the flow volume control device.

An injector for use in the apparatuses of the invention may be an injection valve to be operated manually or an autosampler positioned upstream of the separation channel.

In a preferred embodiment, the injector is an autosampler.

In another preferred embodiment, the injector is arranged in the first flow path downstream of the first valve.

The separation channel of the apparatuses of the invention comprises a first connector (inlet) at a first end and a second connector (outlet) at a second end. The separation channel further comprises another connector by means of which the separation channel is connected to the flow volume control device and which serves to divert the liquid stream created when the cross-flow is applied. The separation channel of the apparatuses of the invention either is a hollow-fiber separation channel or a separation channel for asymmetrical flow field-flow fractionation (AF4).

A hollow-fiber separation channel for use in the apparatuses of the invention comprises one or more hollow-fiber(s) and a housing.

The hollow-fibers for use in the apparatuses of the invention are size-exclusion membranes having a round cross-section. These have an internal diameter (ID) of 0.5 to 1 mm. In a preferred embodiment, the internal diameter of the hollow-fibers used is 1 mm. The hollow-fibers generally have a length of 100 to 370 mm, preferably from 300 to 320 mm and especially preferably 305 mm. The cut-off of the hollow-fibers is from 300 to 100 kDa, preferably 300 Da to 30 kDa and especially preferably 10 kDa. Regenerated cellulose, polyester sulfone (PES) or polyvinylidene fluoride (PVDF) is preferably used as the material for the hollow-fibers.

The hollow-fibers for use in the separation channel of apparatuses of the invention are located in an encapsulated housing (hollow-fiber housing). This has one connector each for the inlet and the outlet of the solvent and another connector for the flow volume control device.

A hollow-fiber and the housing in which the hollow-fiber is located form a hollow-fiber separation channel.

In addition to one, it is also possible to use two, three, four, five, six or more, for example up to 10, up to 20 up to 100 or up to 500 equal hollow-fibers or hollow-fiber separation channels, arranged in parallel. These are combined to form a separation module.

Parallel operation is carried out either by introducing the desired number of hollow-fibers into a single housing so that a suitable hollow-fiber separation channel has more than one hollow-fiber or by use of several hollow-fiber separation channels each of which contains only one hollow-fiber.

Using several hollow-fibers or hollow-fiber separation channels arranged in parallel permits the injection of larger amounts of the sample or a higher sample load in the apparatus of the invention.

It is preferred to use only one or two equal hollow-fiber(s) arranged in parallel or only one hollow-fiber separation channel or two equal hollow-fiber separation channels arranged in parallel. It is especially preferred to use two equal hollow-fibers or hollow-fiber separation channels arranged in parallel.

In another especially preferred embodiment, one hollow-fiber separation channel with two equal hollow-fibers arranged in parallel and contained in one housing is used.

Conventional AF4 separation channels comprising a carrier, a frit, a semi-permeable membrane, a spacer and a cover may be used as the AF4 separation channel to be employed in the apparatuses of the invention. In another embodiment, the frit and the semi-permeable membrane may also be formed in one piece. Separation channels of this kind are described in EP 1 879 025 A1, for example.

The semi-permeable membranes for use in an AF4 separation channel of the apparatuses of the invention are size exclusion membranes. The cut-off of the semi-permeable membranes is at 300 Da to 100 kDa, preferably at 300 Da to 30 kDa, and especially preferably at 10 kDa. It is preferred to use regenerated cellulose, polyether sulfone (PES) or polyvinylidene fluoride (PVDF) as the material for the semi-permeable membranes.

In addition to the first connector (inlet), the second connector (outlet) and the additional connector for the flow volume control device, an AF4 separation channel for use in the apparatuses of the invention may comprise a further (third) connector between the first end and the second end of the separation channel. Solvent is pumped into the separation channel during focusing of the sample through this third connector. An AF4 separation channel comprising a third connector is used in the above described alternative embodiment of the apparatuses of the invention.

In a preferred embodiment, the separation channel is a hollow-fiber separation channel.

In a further especially preferred embodiment, the hollow-fiber separation channel may comprise one hollow-fiber separation channel or several hollow-fiber separation channels each of which comprises a hollow-fiber housing and one or more hollow-fiber(s).

In a further preferred embodiment, the separation channel is a separation channel for asymmetrical flow field-flow fractionation (AF4).

In a further embodiment, the apparatuses of the invention may comprise both a hollow-fiber separation channel and an AF4 separation channel. In this case, the two separation channels are arranged next to each other, i.e. arranged in parallel, so that solvent flows through the one or the other channel during a measuring operation, as required.

The back-pressure element used in the apparatuses of the invention is either a back-pressure capillary or a back-pressure regulator.

In a particularly preferred embodiment, the back-pressure element is a back-pressure capillary.

The internal diameter and the length of a back-pressure capillary for use in the apparatuses of the invention must be selected such that the back-pressure created by the capillary is always greater than the pressure drop across the separation channel.

The dimensions of the back-pressure capillary are further dependent on the separation method used in each case and the flows selected accordingly during the individual phases of fractionation and are therefore variable. In particular, the dimensions of the back-pressure capillary depend on the volume flow adjusted in each case and remaining the same through the detector(s).

Typical or preferred values are a length of 100 to 500 mm and an internal diameter (ID) of 50 to 200 µm. An internal diameter of 125 µm is especially preferred. It is possible to use any material as the material for the back-pressure capillary which is inert vis-à-vis the respective solvent and the sample to be analyzed. Preferred materials are polyether ether ketone (PEEK), fluorinated ethylene propylene copolymer (FEP), perfluoroalkoxy (PFA), high-purity perfluoroalkoxy (HPFA) and stainless steel (SS).

Any commercially available back-pressure regulator suitable for installation into a field-flow fractionation system and/or an HPLC plant may be employed as the back-pressure regulator for use in the apparatuses of the invention. A suitable back-pressure regulator comprises a stamp which is pressed into a sealing seat by a spring against the direction of the flow.

The volume flow caused by the pump generates a pressure of the liquid. This presses against the stamp. If the force acting on the stamp is smaller than the counter-force pre-adjusted by the spring, the stamp remains in its seat and the back-pressure regulator remains closed. If the pressure of the liquid increases sufficiently, the force acting on the stamp also increases until the force of the spring is overcome. As a result, the stamp moves from its seat and the liquid path is opened. Depending on the volume flow, the stamp is pressed out of its seat to a greater or lesser extent so that the opening width varies depending on the force generated by the volume flow and acting on the stamp.

If it is intended to direct a solvent through the second flow path, for example during focusing, the first and the second valves of the apparatuses of the invention are automatically opened and closed at a high clock frequency in an adjustable time ratio; at all times, only one valve is open and the respective other valve is closed, with the result that the volume flow is divided between the first and the second flow path in accordance with the time ratio.

Detector(s) that may be used in the apparatuses of the invention may be any detectors that are known in the field of field-flow fractionation or high-performance liquid chromatography (HPLC). Examples are UV detectors, refractive index (RI) detectors, multi-angle light scattering detectors, mass spectrometers, fluorescence detectors, ICP mass spectrometers, dynamic light scattering detectors (DLS), and small-angle X-ray scattering (SAXS) detectors.

In a preferred embodiment, the detector(s) is/are a UV detector, of refraction index (RI) detector and/or a (multi-angle) light scattering detector.

In the first embodiment of the apparatuses of the invention, the first flow volume splitting device is suitable to split the volume flow generated by the pump into a first flow path connecting the pump to the first connector of the separation channel and a second flow path connecting the pump to the second connector of the separation channel. The first valve and the injector are arranged in the first flow path. The second flow volume splitting device is arranged inside the second flow path and is suitable to split the volume flow of the second flow path between the second connector of the separation channel and the detector(s). The second valve is arranged in the second flow path between the first flow volume splitting device and the second flow volume splitting device. The back-pressure element is arranged in a third flow path connecting the second flow volume splitting device and the detector(s). The flow volume control device is arranged in a fourth flow path connected to the separation channel via a further connector. The waste container(s) is/are arranged behind the detector(s) and the flow volume control device.

In the alternative embodiment of the apparatuses of the invention, the flow volume splitting device is suitable to split the volume flow generated by the pump into a first flow path connecting the pump to the first connector of the AF4 separation channel and a second flow path connecting the pump to the third connector of the AF4 separation channel. The first valve and the injector are arranged in the first flow path. The second valve is arranged in the second flow path between the flow volume splitting device and the third connector of the AF4 separation channel. The back-pressure element is arranged in a third flow path connecting the second connector of the separation channel to the detector(s). The flow volume control device is arranged in a fourth flow path connected to the AF4 separation channel via a further connector. The waste container(s) is/are arranged behind the detector(s) and the flow volume control device.

The flow scheme of the apparatuses of the invention as described above is achieved by installing the first valve in the first flow path and the second valve in the second flow path. This makes it possible to do without commercial mass flow controllers for flow volume control. In particular, this solves the problem known from the prior art in connection with the use of mass flow controllers with regard to the limited dynamic range for the flow rates, the delayed response time for flow rate regulation and the limited operating pressure range and flow rate sensitivity. All in all, this permits realization of a programmable focus flow with a concomitant reduction of components which decreases both cost and the risk of failure.

In a first especially preferred embodiment, the apparatuses of the invention comprise one or more reservoir(s), pump, a first flow volume splitting device, two micro-valves with switching times each in the range from 200 to 400 µs for flow control, an autosampler as the injector, a hollow-fiber or AF4 separation channel having a first connector at a first end and a second connector at a second end, a second flow volume splitting device, a back-pressure capillary as the back-pressure element, a UV detector, a refractive index (RI) detector and/or a (multi-angle) light scattering detector as the detector(s), a syringe pump system comprising two syringes operating in the pendulum mode as the flow volume control device and one or more waste container(s).

The apparatuses of the invention according to the especially preferred embodiment described above are characterized by the following flow scheme:

The first flow volume splitting device is suitable to split the volume flow generated by the pump into a first flow path connecting the pump to the first connector of the hollow-fiber or AF4 separation channel and a second flow path connecting the pump to the second connector of the hollow-fiber or AF4 separation channel. The first micro-valve and the autosampler are arranged in the first flow path, the autosampler being arranged downstream of the first micro-valve. The second flow volume splitting device is arranged in the second flow path and is suitable to split the volume flow of the second flow path between the second connector of the hollow-fiber or AF4 separation channel and the detector(s). The second micro-valve is arranged in the second flow path between the first flow volume splitting device and the second flow volume splitting device. The back-pressure capillary is arranged in a third flow path connecting the second flow volume splitting device and the UV detector, refractive index (RI) detector and/or (multi-angle) light scattering detector used as the detector(s). The syringe pump system is arranged in a fourth flow path connected to the hollow-fiber or AF4 separation channel via a further connector. The waste container(s) is/are arranged behind the detector(s) and the syringe pump system.

In an alternative, especially preferred embodiment, the apparatuses of the invention comprise one or more reservoir(s), a pump, a first flow volume splitting device, two micro-valves with switching times in the range from 200 to 400 µs each for flow control, an autosampler as the injector, an AF4 separation channel having a first connector at a first end, a second connector at a second end and a third connector between the first end and the second end of the separation channel, a back-pressure capillary as the back-pressure element, a UV detector, a refractive index (RI) detector and/or (multi-angle) light scattering detector as the detector(s), a syringe pump system with two syringes operating in a pendulum mode as the flow volume control device and one or more waste containers.

The apparatuses of the invention according to the alternative, especially preferred embodiment described above are characterized by the following flow scheme:

The first flow volume splitting device is suitable to split the volume flow generated by the pump into a first flow path connecting the pump to the first connector of the AF4 separation channel and a second flow path connecting the pump to the third connector of the AF4 separation channel. The first micro-valve and the autosampler are arranged in the first flow path, the autosampler being arranged downstream of the first micro-valve. The second micro-valve is arranged in the second flow path between the first flow volume splitting device and the third connector of the AF4 separation channel. The back-pressure capillary is arranged in a third flow path connecting the second connector of the AF4 separation channel and the UV detector, refractive index (RI) detector and/or (multi-angle) light scattering detector used as the detector(s). The syringe pump system is arranged in a fourth flow path connected to the AF4 separation channel via a further connector. The waste container(s) is/are arranged behind the detector(s) and the syringe pump system.

It is possible to use all of the preferred and especially preferred embodiments of the apparatuses of the invention as described above in the method of the invention for analyzing a sample by means of field-flow fractionation using the apparatuses of the invention.

A method of the invention is especially preferred wherein
in step (i), a sample is injected into a solvent,
in step (ii), the solvent into which the sample has been injected is flushed into the separation channel with a clocked volume flow via the first connector (inlet) of the separation channel and additional solvent is pumped into the separation channel, again with a clocked volume flow, through the second flow volume splitting device via the second connector (outlet) of the separation channel, wherein by means of the back-pressure element and the second flow volume splitting device, the solvent is divided into a first portion which flows in the direction of the outlet of the separation channel and a second portion which flows in the direction of the detector(s), and
in step (iii), the volume flow to the outlet of the separation channel via the second flow volume splitting device is first reduced to zero and, at the same time, the volume flow to the inlet of the separation channel is increased by the same quantity and the sample is then eluted from the separation channel under the influence of a separation field via the second volume flow splitting device and the back-pressure element and is detected in one or more detector(s), wherein the volume flow and the flow direction of the solvent through the detector(s) remain the same and the strength of the separation field is controlled by means of the flow volume control device connected to the separation channel by a further connector and, at the same time, the volume flow is varied such that the volume flow through the detector(s) remains the same when the strength of the separation field varies.

In an alternative embodiment, a method of the invention is especially preferred wherein
in step (i), a sample is injected into the solvent,
in step (ii), the solvent into which the sample has been injected is flushed into the separation channel with a clocked volume flow via the first connector (inlet) of the AF4 separation channel and additional solvent is pumped into the AF4 separation channel via the third connector of the AF4 separation channel, again with a clocked volume flow, wherein the solvent is split in the AF4 separation channel with the aid of the back-pressure element into a first portion which flows in the direction of the inlet of the AF4 separation channel and a second portion which flows from the second connector (outlet) of the AF4 separation channel in the direction of the detector(s), and
in step (iii), the flow through the third connector of the AF4 separation channel is first switched off and, at the same time, the flow into the inlet of the AF4 separation channel is permanently switched on and the sample is then eluted from the AF4 separation channel under the influence of a separation field via the back-pressure element and detected in the detector/s), wherein the volume flow and the flow direction of the solvent through the detector(s) remain the same and the strength of the separating field is controlled with the aid of the flow volume control device connected to the AF4 separation channel by a further connector and, at the same time, the volume flow is varied such that the volume flow through the detector(s) remains the same when the strength of the separation field varies.

In connection with the present invention, the terms "the same" or "remain(s) the same" when used with regard to a volume flow mean that this volume flow must not vary by more than ±2%, preferably by not more than ±1.2%. For example, a volume flow through the detector(s) of 1 ml/min should not vary by more than 12 µl/min.

In a further especially preferred embodiment of the apparatuses of the invention comprising two valves for flow control, the average flow rate in the first flow path is 0.01 ml/min to 0.5 ml/min in step (i) and step (ii) of the methods of the invention described above, i.e. while the sample is being injected and focused.

The function of the two valves of the apparatuses of the invention for flow control will be explained by an example in the following.

A typical pump flow for focusing in a system for field-flow fractionation is 5 ml/min. This flow is split during focusing between the first and the second flow path. A typical splitting ratio is, for example, a flow of 0.2 ml/min over the first flow path (also called injection flow) and a flow of 4.8 ml/min over the second flow path (also called focus flow). Splitting of the pump flow in the apparatuses of the invention is carried out by the time clocked control of the two valves in the first and second flow path. The two valves are never open at the same time. Instead, only one valve is open and the other valve is closed at all times.

The clocking time of the two valves required for opening and closing, i.e. the cycle time for switching the two valves, is preferably 200 ms.

This permits calculation of the opening times of the valves required for the desired injection flow of 0.2 ml/min and the desired focus flow of 4.8 ml/min by the following equation:

Opening time of the first valve=cycle time*injection flow/(injection flow+focus flow)=200 ms*0.2 ml/min/(0.2 ml/min+4.8 ml/min)=8 ms Opening time of the second valve=cycle time*focus flow/(injection flow+focus flow)=200 ms+4.8 ml/min/(0.2 ml/min+4.8 ml/min)*192 ms The two valves are opened and closed alternately. During the time the first valve is open, i.e., in the present example, for a time period of 8 ms, the entire flow of 5 ml/min generated by the pump thus flows through the first flow path and moves the sample for a short time in the direction of the channel outlet. After 8 ms, the first valve in the first flow path closes while, at the same time, the second valve in the second flow path is opened for the calculated 192 ms. The entire flow from the pump now flows through the second flow path and is split between the channel and the detector(s). The second valve is then closed and the first valve reopened. Alternate opening and closing of the valves for 8 and, respectively, 192 ms takes place in accordance with the respective separation method and may, for example, occur over a period of 0.1 min to 120 min or 0.1 min to 60 min or 0.5 min to 30 min. This inhibits the movement of the sample in the direction of the channel outlet and the sample is focused in the channel. In other words, an effect similar to the continuous splitting of the volume flow generated by the pump between the first and the second flow path as known from the prior art is achieved by sequential switching of the valves. The separation of the monomers and the trimers of the model protein (BSA, bovine serum albumin with a molecular weight of the monomer of 66 kDa) shown in FIG. 3 proves that the apparatus of the invention and, respectively, the method of the invention are suitable for analyzing a sample by means of field-flow fractionation. Given the problems resulting from pressure variations while the respective valves are being switched which are known in systems for field-flow fractionation this was not expected.

After injection and focusing of the sample, i.e. during elution in step (iii), the two valves are no longer needed for flow control. The first valve in the first flow path then remains open permanently, while the second valve in the second flow path remains closed permanently.

WAYS FOR CARRYING OUT THE INVENTION

Figure 1:
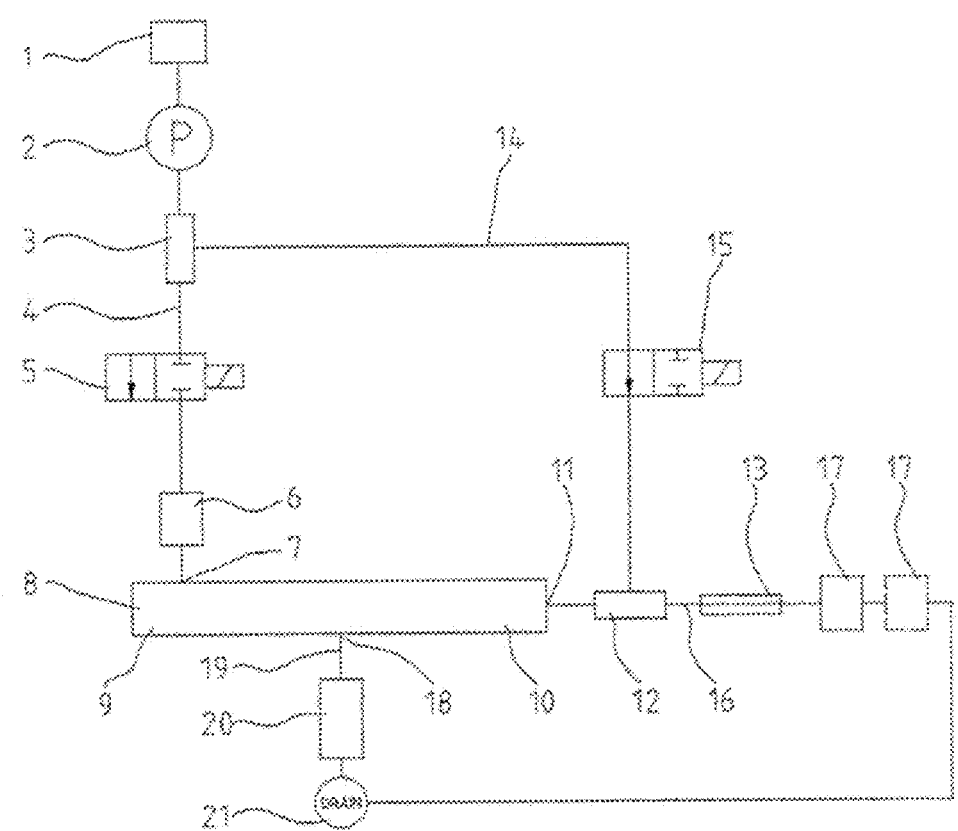
FIG. 1 shows the schematic design of an apparatus of the invention according to the first preferred embodiment.

In the following, preferred embodiments of the apparatuses of the invention will be explained with reference to the attached drawings and the reference numerals used there.

FIG. 1 shows the schematic design of an apparatus for field-flow fractionation according to the invention. Having passed a reservoir (1) and a pump (2), the volume flow is split via a T-connector (3) into a first flow path (4) and a second flow path (14). The first flow path (4) is initially guided to a first valve (5) and then, via an injector (6), to a first connector (inlet) (7) at a first end (9) of the separation channel (8). The separation channel can either be a hollow-fiber separation channel or an AF4 separation channel.

The second flow path (14) is guided to a second T-connector (12) via a second valve (15). This T-connector splits the volume flow between a second connector (outlet) (11) at a second end (10) of the separation channel (8) and a third flow path (16) which is guided to the detector(s) (17) via a back-pressure element (13).

The back-pressure element (13) is preferably a back-pressure capillary which, depending on the flow rate applied, generates a suitable back-pressure on the system. The back-pressure is necessary to apply pressure to the separation channel (8) and thus to the flow volume control device (20) which is connected to the separation channel (8) via a fourth flow path (19) and a further connector (18) so that the separation channel (8) can work. The flow volume control device (20) controls/regulates the flow through the size exclusion membrane of the separation channel (8), i.e. the separating field/the cross-flow, and thus influences the separation performance of the field-flow fractionation apparatus.

The solvent is removed from the flow volume control device (20) and the detector(s) (17) of the apparatus, for example into the waste container (21).

Separation of the sample by means of the apparatuses of the invention shown in FIG. 1 consists of three steps.

In the first step, the sample is injected into the system by the injector (6) and conveyed to the separation channel (8).

In the second step, the sample is focused at the front end of the separation channel (8). During this step, a solvent is conveyed into the separation channel (8) at a flow rate in the range from 0.01 ml/min to 0.5 ml/min along the first flow path (4) via the first valve (5) through the injector (6). At the same time, a further, suitably larger volume flow is conveyed through the second flow path (14) via the second valve (15). Owing to the back-pressure generated by means of the back-pressure element (13), one portion of the solvent flows via the second T-connector (12) in the opposite direction through the outlet (11) into the separating channel (8), while another portion of the solvent flows in the direction of the third flow path (16). As a result, the sample is focused at the front end of the separation channel (8). Meanwhile, the flow volume control device (20) is active and is controlled in such a manner that the volume flow through the flow volume control device (20) is somewhat smaller than the volume flow from the pump (2) into the system. Thus, a controlled volume flow in the direction of the detector(s) (17) results in the third flow path (16). By means of the back-pressure element (13), the back-pressure described above which is necessary for the operation of the flow volume control device (20) is generated in the separation channel (8).

In the third step, the sample injected into the separation channel (8) via the injector (6) is eluted from the separation channel (8) after focusing. For this purpose, the volume flow through the second flow path (14) must be stopped. At the same time, the volume flow through the first flow path (4) must be increased by the quantity of the previous volume flow through the second flow path (14) so as to ensure a constant volume flow in the third flow path (16) and thus through the detector(s) (17). At the same time, a separation field (cross-flow) is applied in the separation channel (8) which is generated by the flow volume control device (20). During elution, the volume flow conveyed by the pump (2) is controlled depending on the strength of the cross-flow in such a manner that the volume flow through the third flow path (16) and hence through the detector(s) (17) remains constant.

The flows described for the individual steps are time-regulated by suitable software.

As described above, mass flow controllers are limited in the dynamic flow rate range. In the novel flow scheme using just one pump and two valves according to the present invention, this problem is avoided altogether. While the sample is being injected and focused, the flow in the first (4) and the second (14) flow path is time-controlled in an alternating manner with the aid of the two valves (5, 15), the opening time of the first valve being shorter than the opening time of the second valve and the average flow rate in the first flow path (4) being 0.01 ml/min to 0.5 ml/min. After the sample has been injected and focused, i.e. during elution, the first valve (5) in the first flow path (4) remains permanently open, while the second valve (15) in the second flow path (14) remains permanently closed. As a result, the entire volume flow conveyed by the pump (2) reaches the separation channel (8) via the first flow path (4). Regulation of the flow through the valves (5, 15) switched in sequence is no longer necessary since the solvent reaches the system only through the first flow path (4) and the flow rate is determined by the pump (2).

Figure 2:
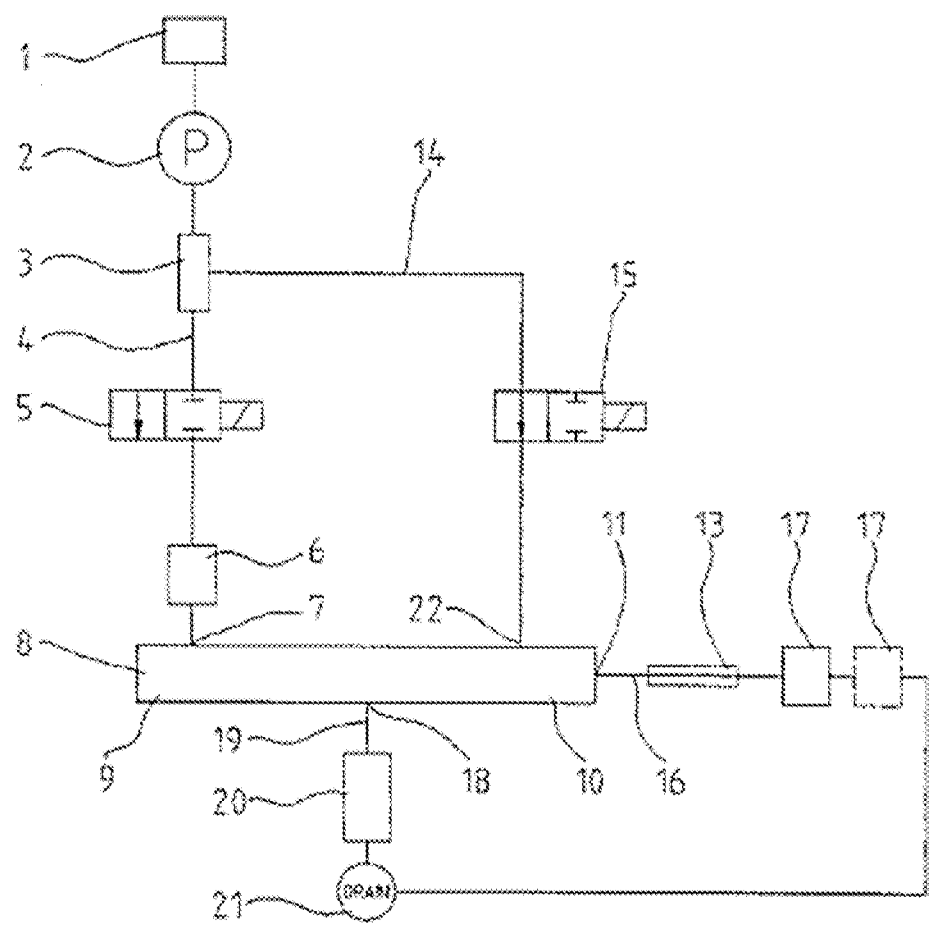
FIG. 2 shows the schematic design of an apparatus of the invention according to the alternative preferred embodiment.
Figure 3:
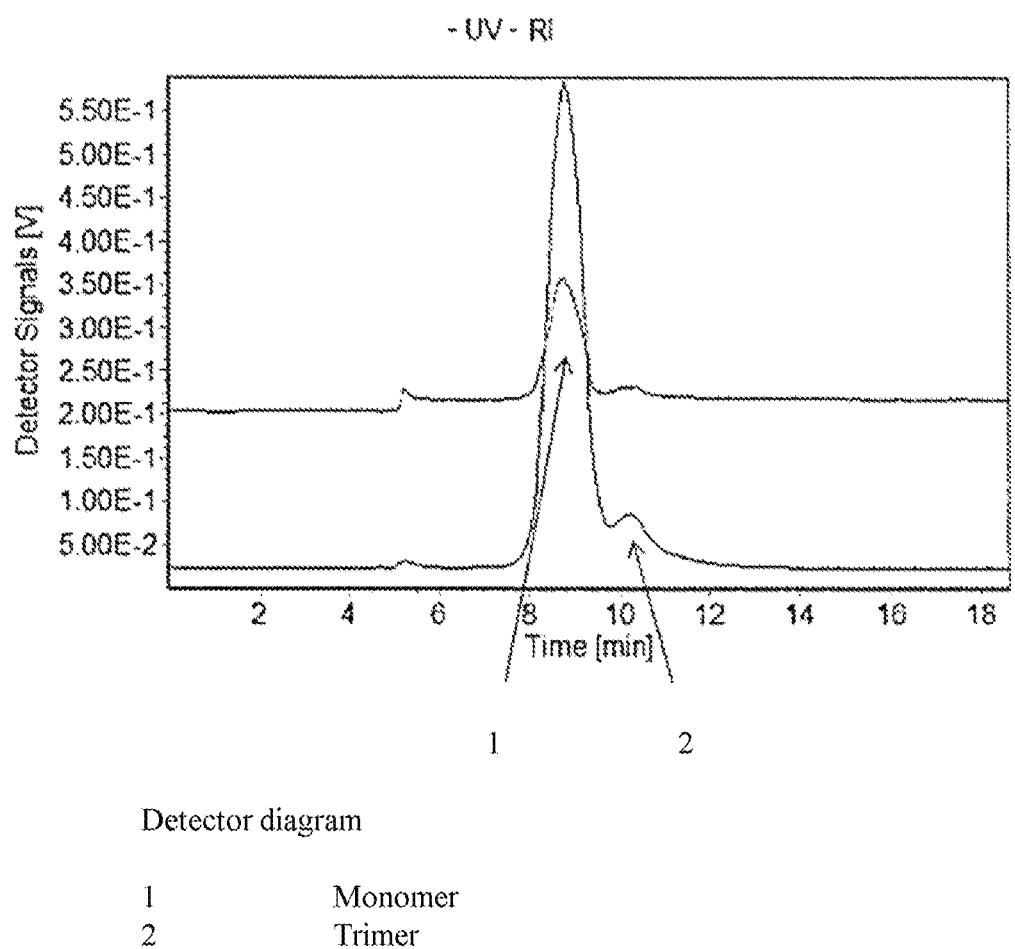
FIG. 3 shows the result of an exemplary protein measurement using an apparatus of the invention according to the alternative preferred embodiment.

FIG. 2 shows the schematic design of an apparatus for field-flow fractionation according to the alternative embodiment of the invention. Once it has passed a reservoir (1) and a pump (2), the volume flow is divided into a first flow path (4) and a second flow path (14) via a T-connector (3). The first flow path (4) is initially guided to a first valve (5). The first flow path then leads via an injector (6) to a first connector (inlet) (7) at a first end (9) of the separation channel (8). The separation channel is an AF4 separation channel.

The second flow path (14) is guided via a second valve (15) to a third connector (22) between the first end (9) and a second end (10) of the separation channel (8).

A third flow path (16) leads from the second connector (outlet) (11) at the second end (10) of the separation channel (8) to the detector(s) (17) via a back-pressure element (13).

As far as the function and the effect of the back-pressure element (13) and the second valve (15) integrated into the second flow path (14) and the flow volume control device (20) in the fourth flow path (19) are concerned, the apparatus shown in FIG. 2 corresponds to that shown in FIG. 1. The corresponding explanations regarding FIG. 1 thus also apply to FIG. 2.

The solvent is removed from the flow volume control device (20) and the detector(s) (17) of the apparatus, for example into a waste container (21).

Separation of a sample by means of the apparatuses of the invention shown in FIG. 2 consists of three steps.

In the first step, the sample is injected into the system via the injector (6) and conveyed to the separation channel (8).

In the second step, the sample is focused at the front end of the separation channel (8). During this step, solvent is conveyed into the separation channel (8) at a flow rate in the range from 0.01 ml/min to 0.5 ml/min along the first flow path (4) via the first valve (5) through the injector (6). At the same time, a further, suitably larger volume flow is conveyed through the second flow path (14) via the second valve (15), and the solvent flows into the separation channel (8) through the third connector (22). Due to the back-pressure generated with the aid of the back-pressure element (13), the solvent stream is divided in such a manner that one portion of the solvent flows through the outlet (11) from the separation channel (8) in the direction of the third flow path (16) and another portion of the solvent flows through the separation channel (8) in the opposite direction. As a result, the sample is focused at the front end of the separation channel (8). Meanwhile, the flow volume control device (20) is active and is controlled in such a manner that the volume flow through the flow volume control device (20) is somewhat smaller than the volume flow from the pump (2) into the system. Thus, a controlled volume flow in the direction of the detector(s) (17) results in the third flow path. Due to the back-pressure element (13), the back-pressure described above, which is necessary for the operation of the flow volume control device (20), is generated in the separation channel (8).

In the third step, the sample injected into the separation channel (8) via the injector (6) is eluted from the separation channel (8) after focusing. For this purpose, the volume flow through the second flow path (14) must be stopped. At the same time, the volume flow through the first flow path (4) must be increased by the quantity of the previous volume flow through the second flow path (14) so as to ensure a constant volume flow in the third flow path (16) and thus through the detector(s) (17). At the same time, a separation field (cross-flow) is applied in the separation channel (8) which is generated by the flow volume control device (20). During elution, the volume flow conveyed by the pump (2) is controlled depending on the strength of the cross-flow in such a manner that the volume flow through the third flow path (16) and hence the through the detector(s) (17) remains constant.

The flows described for the individual steps are time-regulated by suitable software.

As far as the function and the effect of the two valves (5, 15) as compared to the use of a mass flow regulator are concerned, the apparatus shown in FIG. 2 corresponds to the apparatus shown in FIG. 1. The corresponding explanations regarding FIG. 1 thus also apply to FIG. 2.

LIST OF REFERENCE NUMERALS

1 reservoir
2 pump
3 first flow volume splitting device
4 first flow path
5 first valve
6 injector
7 first connector (inlet)
8 separation channel
9 first end
10 second end
11 second connector (outlet)
12 second flow volume splitting device
13 back-pressure element
14 second flow path
15 second valve
16 third flow path
17 detector(s)
18 additional connector
19 fourth flow path
20 flow volume control device
21 waste container
22 third connector

The invention claimed is:

1. An apparatus for field-flow fractionation, comprising one or more reservoirs, a pump, a first flow volume splitting device, a first valve, an injector, a separation channel with a first connector at a first end and a second connector at a second end, a second flow volume splitting device, a second valve, a back-pressure element, one or more detectors, a flow volume control device and one or more waste containers, wherein
the first flow volume splitting device is suitable to split the volume flow generated by the pump into a first flow path connecting the pump to the first connector of the separation channel and a second flow path connecting the pump to the second connector of the separation channel,
the injector is arranged in the first flow path,
the second flow volume splitting device is arranged within the second flow path and is suitable to split the volume flow of the second flow path between the second connector of the separation channel and the one or more detectors,
the back-pressure element is arranged in a third flow path connecting the second flow volume splitting device and the one or more detectors,
the flow volume control device is arranged in a fourth flow path which is connected to the separation channel via a further connector; and
the one or more waste containers is arranged behind the one or more detectors and the flow volume control device, characterized in that the first valve is arranged in the first flow path between the first flow volume splitting device and the injector, and
the second valve is arranged in the second flow path between the first flow volume splitting device and the second flow volume splitting device;
wherein the first valve and the second valve are microvalves having switching times in the range from 200 to 400 µs.

2. The apparatus according to claim 1, wherein the flow rate in the first flow path during injection and focusing of the sample is 0.01 ml/min to 0.5 ml/min.

3. The apparatus according to claim 1, wherein the separation channel is a hollow-fiber separation channel or a separation channel for asymmetrical flow field-flow fractionation (AF4).

4. The apparatus according to claim 3, wherein the hollow-fiber separation channel may comprise one hollow-fiber separation channel or several hollow-fiber separation channels, each comprising a hollow-fiber housing and one or more hollow-fibers.

5. The apparatus according to claim 1, wherein the injector in the first flow path is arranged downstream of the first valve.

6. The apparatus according to claim 1, wherein the injector is an injection valve to be operated manually or an autosampler.

7. The apparatus according to claim 1, wherein the flow volume control device is a syringe pump system comprising two syringes operating in a pendulum mode.

8. The apparatus according to claim 1, wherein each of the first flow volume splitting device and the second flow volume splitting device is a T-connector.

9. The apparatus according to claim 1, wherein the back-pressure element is a back-pressure capillary.

10. The apparatus according to claim 1, wherein the one or more detectors is a UV detector, a refractive index (RI) detector and/or a (multi-angle) light scattering detector.

11. The apparatus according to claim 1, wherein the apparatus further comprises an autosampler as the injector, a hollow-fiber or an AF4 separation channel as the separation channel, a back-pressure capillary as the back-pressure element, a UV detector, a refractive index (RI) detector and/or a (multi-angle) light scattering detector as the one or more detectors and a syringe pump system with two syringes operating in a pendulum mode as the flow volume control device.

12. A method for analyzing a sample by means of field-flow fractionation using the apparatus according to claim 1 and comprising the following steps:
(i) injection of a sample into the separation channel using a solvent,
(ii) focusing the sample with the aid of the solvent in the separation channel, and
(iii) elution of the sample with the solvent from the separation channel under the influence of a separation field and detection of the fractionated sample with one or more detectors,
characterized in that the first valve and the second valve are opened and closed alternately during focusing in step (ii), only one valve being open at a time and the other valve being closed, and the opening time of the first valve being shorter than the opening time of the second valve.

13. The method according to claim 12, wherein the flow rate in the first flow path is 0.01 ml/min to 0.5 ml/min in step (i) and step (ii).

14. The method according to claim 13, wherein during elution in step (iii), the first valve in the first flow path is permanently open, while the second valve in the second flow path is permanently closed.

15. An apparatus for field-flow fractionation, comprising one or more reservoirs, a pump, a flow volume splitting device, a first valve, an injector, a separation channel for asymmetrical flow field-flow fractionation (AF4) having a first connector at a first end, a second connector at a second end and a third connector between the first end and the second end of the separation channel, a second valve, a back-pressure element, one or more detectors, a flow volume control device and one or more waste containers, wherein the flow volume splitting device is suitable to split the volume flow generated by the pump into a first flow path connecting the pump to the first connector of the separation channel and a second flow path connecting the pump to the third connector of the separation channel, the injector is arranged in the first flow path, the back-pressure element is arranged in a third flow path connecting the second connector of the separation channel to the one or more detectors, the flow volume control device is arranged in a fourth flow path connected to the separation channel via a further connector, and the one or more waste containers is arranged behind the one or more detectors and the flow volume control device, characterized in that the first valve is arranged in the first flow path between the flow volume splitting device and the injector, and the second valve is arranged in the second flow path between the flow volume splitting device and third connector of the separation channel;

wherein the first valve and the second valve are microvalves having switching times in the range from 200 to 400 µs.

16. The apparatus according to claim 15, wherein the apparatus further comprises an autosampler as the injector, an AF4 separation channel as the separation channel, a back-pressure capillary as the back-pressure element, a UV detector, a refractive index (RI) detector and/or a (multi-angle) light scattering detector as the one or more detectors and a syringe pump system with two syringes operating in the pendulum mode as the flow volume control device.

17. The apparatus according to claim 15, wherein the flow rate in the first flow path during injection and focusing of the sample is 0.01 ml/min to 0.5 ml/min.

18. The apparatus according to claim 15, wherein the injector in the first flow path is arranged downstream of the first valve.

19. The apparatus according to claim 15, wherein the injector is an injection valve to be operated manually or an autosampler.

20. The apparatus according to claim 15, wherein the flow volume control device is a syringe pump system comprising two syringes operating in a pendulum mode.

21. The apparatus according to claim 15, wherein the back-pressure element is a back-pressure capillary.

22. The apparatus according to claim 15, wherein the one or more detectors is a UV detector, a refractive index (RI) detector and/or a (multi-angle) light scattering detector.

23. A method for analyzing a sample by means of field-flow fractionation using the apparatus according to claim 15 and comprising the following steps:

(i) injection of a sample into the separation channel using a solvent, (ii) focusing the sample with the aid of the solvent in the separation channel, and (iii) elution of the sample with the solvent from the separation channel under the influence of a separation field and detection of the fractionated sample with one or more detectors, characterized in that the first valve and the second valve are opened and closed alternately during focusing in step (ii), only one valve being open at a time and the other valve being closed, and the opening time of the first valve being shorter than the opening time of the second valve.

24. The method according to claim 23, wherein the flow rate in the first flow path is 0.01 ml/min to 0.5 ml/min in step (i) and step (ii).

25. The method according to claim 24, wherein during elution in step (iii), the first valve in the first flow path is permanently open, while the second valve in the second flow path is permanently closed.

* * * * *